CHRYSANTHEMUM PLANT
Filed Nov. 30, 1970 2 Sheets-Sheet 1
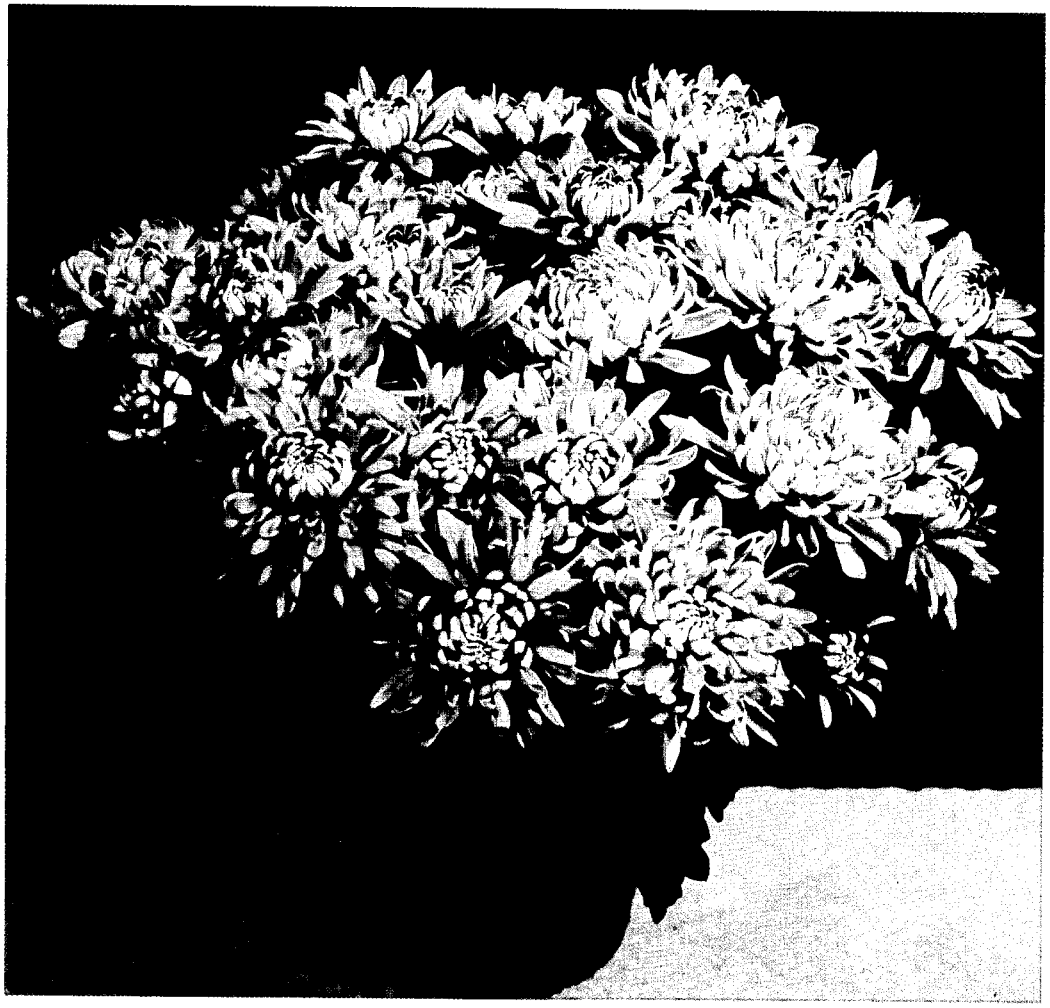
INVENTORS
WALTER H. JESSEL, JR.,
WILLIAM E. DUFFETT
BY
Oberlin, Maky, Donnelly & Renner
ATTORNEYS CHRYSANTHEMUM PLANT
Filed Nov. 30, 1970 2 Sheets-Sheet 2
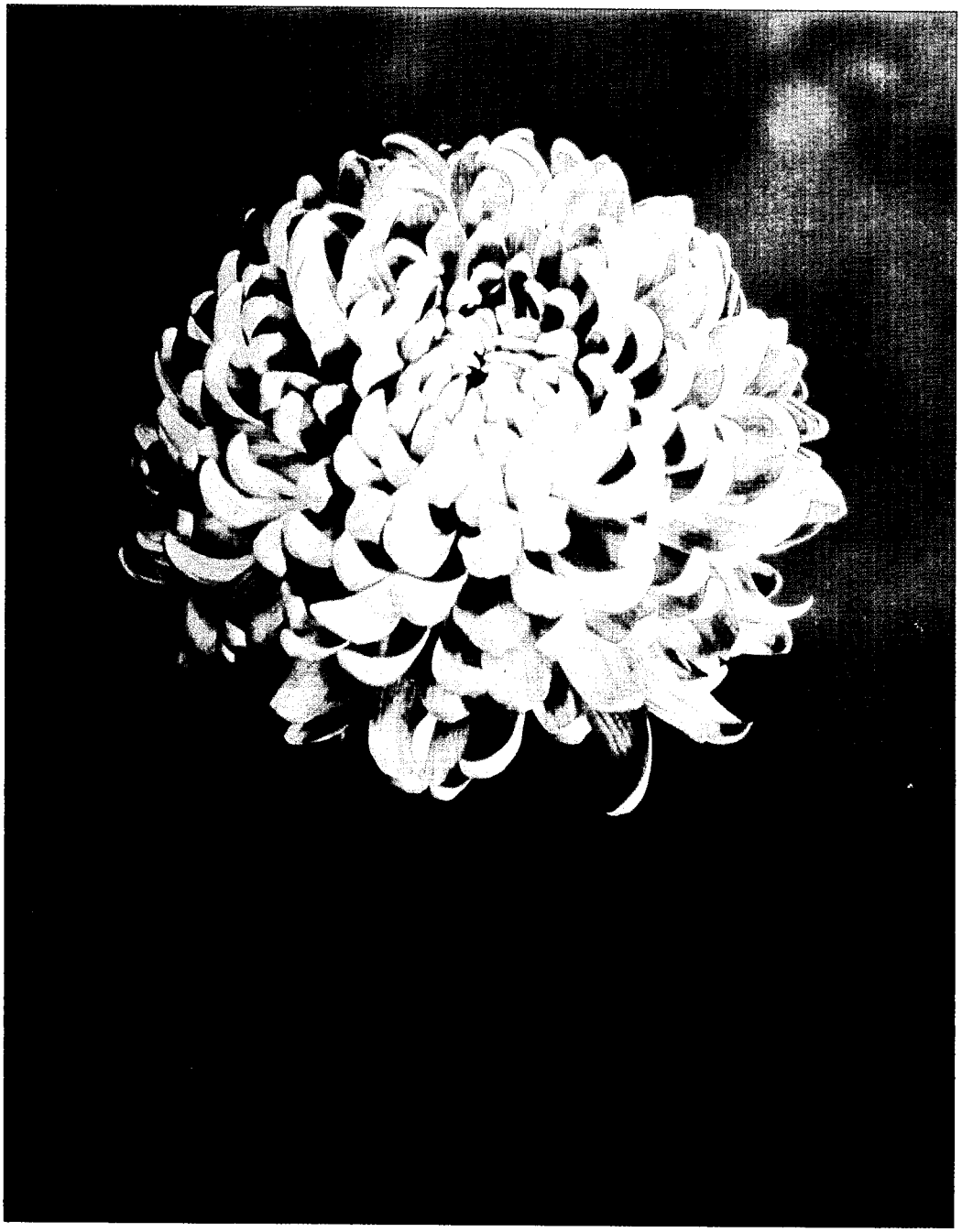

United States Patent Office

Plant Pat. 3,236

Patented July 18, 1972

3,236

CHRYSANTHEMUM PLANT

Walter H. Jessel, Jr., Doylestown, and William E. Duffett, Akron, Ohio, assignors to Yoder Brothers, Inc., Barberton, Ohio

Filed Nov. 30, 1970, Ser. No. 93,922

Int. Cl. A01h *5/00*

U.S. Cl. Plt.—79 1 Claim

The present invention comprises a new and distinct cultivar of chrysanthemum plant which is a seedling of #61865-1×#63969-1, with both parents being unpatented and identified for breeding purposes by the above numbers.

The new cultivar was selected from the progeny of the designated cross and when asexually reproduced by cuttings has been found to retain its distinctive characteristics through successive propagations.

An important feature of the new cultivar is its versatility. The cultivar can be grown either as a pot mum or a standard cut flower, depending on which established growing procedures are followed. To our knowledge, the new cultivar is the only bronze summer flowering crysanthemum that has this dual capacity.

The unique features of the new cultivar can perhaps best be seen by comparing the same to commercially well-known pot mum and standard crysanthemums, respectively. With respect to its pot mum form, the new cultivar is similar to the unpatented but commercially well-known pot mum cultivar Orange Bowl in its orange bronze coloration but differs therefrom by the following characteristics:

(1) Wildfire has a 9 week response as compared with the 10 week response of Orange Bowl.

(2) The flower color of the new cultivar is more intense, and the flowers are ¼" larger in the tight or opening stage but are smaller when fully open than the flowers of Orange Bowl.

(3) Wildfire has a more incurved flower, and has larger and more deeply indented foliage with less serration of the leaf margin.

(4) Wildfire has more prominent stipules.

(5) Wildfire has a shorter bench life.

(6) Wildfire is more efficient to the grower (9 week tall treatment as compared with a 10 week short or medium treatment of Orange Bowl) which is a saving in crop time of two to three weeks depending on treatment.

The new cultivar when grown as a pot mum in the vicinity of Barberton, Ohio, has a response period of approximately 9 weeks, and the following detailed description is based on observations made of the new cultivar grown as a pot mum in a greenhouse in Barberton, Ohio. The response time, blooming period, color, and total vigor may vary significantly with varying environmental conditions such as temperature, day length, and light intensity. Suggested flowering in the northern and western United States is from May through October; in coastal California, May through October; in Florida, December through April, and in the southern United States, March through November.

In the accompanying drawings, Sheet 1 shows the unique characteristics of the new cultivar displayed in the form of a pot mum. Sheet 2 illustrates the new cultivar as a standard or cut flower. It will be noted that there appears to be a difference in flower color between the pot mum and standard photographs. This apparent difference is for two reasons. One, the photograph of the standard was taken in a high light, high temperature period of the year when the flower is more incurved and the reverse side of the petals therefore more visible. The overall tone of the flower is therefore a lighter bronze. The pot mum, on the other hand, was photographed very late in the fall, with the top color of the petals being darker than at other periods of the year. Moreover, the pot mum is more heavily cropped, and there is less reversing because the flower is more semi-incurved in form.

In the following description of Wildfire as a pot mum, color references are to the Munsell Color Book, 1963 edition, and comparisons have been made with Orange Bowl. Some difficulty was encountered in precisely determining the various bronze tones of the cultivars compared, and the indicated colors represent the closest available color key.

BOTANICAL CLASSIFICATION

*Chrysanthemum morifolium*

| | Wildfire | Orange Bowl |
|---|---|---|
| Bloom: | | |
| Size | 5¼" | 5". |
| Fully expanded | 5¾" | 6". |
| Borne | Singly on disbudded stems. | Singly on disbudded stems. |
| Stems | Strong | Strong. |
| Form | Generally semi-incurved, becoming increasingly decorative as daylength shortens and overall temperatures become lower. | Irregular, decorative. |
| Permanence | 10-14 days | 15-20 days. |
| Color: | | |
| Center of flower. | Light bronze, 5Y7/8 to golden bronze, 5Y7/10. | Greenish yellow, 7.5Y8/10 to yellow, 5Y8/10. |
| Base of petals. | Red bronze, 5R3/8 to light bronze, 2.5Y6/8 over yellow 5Y8.5/10. | Bronze, 7.5YR5/8 over dark yellow, 2.5Y8.5/12. |
| Inside of petals. | do | Bronze, 7.5YR5/8 over dark yellow, 2.5Y8.5/12 to light bronze, 2.5Y7/8 over dark yellow, 5Y8.5/12. |
| Reverse of petals. | Light bronze, 5Y7/8 to golden bronze, 5Y7/10. | Yellow, 5Y8/10 to light yellow, 5Y8/8. |
| Tonality from a distance. | Orange bronze | Orange bronze to golden yellow depending on temperatures at finishing time. |
| Discoloration. | Golden bronze | Golden yellow. |
| Petals: | | |
| Texture | Smooth | Smooth. |
| Appearance and form. | Open at base, broad keel tapering to a hooded point. | Open at base, broadens quickly, shallow ridged keel, tapering to a blunt point. |
| Arrangement | Composite, whorled on a single receptacle. | Composite, whorled on a single receptacle. |
| Persistence | Resist shatter | Resist shatter. |
| Fragrance | Typical chrysanthemum. | Typical chrysanthemum. |
| Reproductive organs: | | |
| Stamen, anthers | None to 30 | None. |
| Pollen | None to scant | Do. |
| Arrangement | Clustered in center of flower, if present. | Clustered in center of flower, if present. |
| Styles | Present both ray and disc florets. | Present both ray and disc florets. |
| Length | Short | Short. |
| Ovaries | At the base of petal attached to receptacle. | At the base of petal attached to receptacle. |
| Plant: | | |
| Form | Herbaceous | Herbaceous. |
| Growth | Semi-upright | Spreading. |
| Height | 11"-13" | 12½"-14½". |
| Spread | 8" | 10". |
| Foliage: | | |
| Top side | Dark green, 10GY3/4 | Dark green, 10GY3/4. |
| Size | 5¼" long, 2½" wide | 4½" long, 2¾" wide. |
| Quantity | Numerous | Numerous. |
| Shape | Spatulate lobed | Spatulate lobed. |
| Texture | Smooth | Smooth. |
| Ribs and veins | Prominent | Prominent. |
| Edge | Deeply indented | Moderately indented. |
| Serration | Very slight | Finely serrated. |
| Underside | Light green, 10GY5/4 | Light green, 7.5GY5/4. |
| Stipules | Prominent | Small. |

As a standard, the new cultivar can be compared with the unpatented but well-known bronze standard Detroit News, having the same 9 week response of Detroit News, but differing from Detroit News when grown as a standard by the following characteristics:

(1) A longer recommended flowering period in all areas of the United States, thereby providing a longer period of value.

(2) ¼″ larger flowers.

(3) Broader, flatter petals with less incurved form.

(4) Longer keeping quality.

(5) More intense orange bronze in color.

(6) Under high temperature, high light conditions Wildfire provides greater color retention and, in fading, has a darker, smoother, more attractive golden bronze color than the faded color of Detroit News under identical conditions.

(7) 7″ shorter habit.

(8) Somewhat lighter colored and less brittle foliage.

(9) More prominent stipules.

The new cultivar when grown as a standard in the vicinity of Barberton, Ohio, has a response period of approximately 9 weeks, and the following detailed description is based on observations made of the new standard cultivar grown in a greenhouse in Barbeton, Ohio. The response time, blooming period, color, and total vigor may vary significantly with varying environmental conditions such as temperature, day length, and light intensity. Suggested flowering as a standard in the nothern and western United States is from June through October; in coastal California, June through October; in Florida, December through April; and in the southern United States; May through November.

As above, color references are to the Munsell Color Book, 1963 edition, and comparions have been made with the cultivar Detroit News.

BOTANICAL CLASSIFICATION

*Chrysanthemum morifolium*

| | Wildfire | Detroit News |
|---|---|---|
| Bloom: | | |
| Size | 5¼″ | 5″. |
| Fully expanded | 5¾″ | 5½″. |
| Borne | Terminal on disbudded plant. | Terminal on disbudded plant. |
| Stems | Strong | Strong. |
| Form | Semi-incurve | Incurve. |
| Permanence | 10–14 days | 7–10 days. |
| Color: | | |
| Center of flower. | Light bronze, 5Y7/8 to golden bronze, 5Y7/10. | Yellow bronze, 2.5Y6/10. |
| Base of petals. | Red bronze, 5R3/8 to light bronze, 2.5Y6/8 over yellow, 5Y8.5/10. | Yellow, 7.5Y8.5/10. |
| Inside of petals. | do | Bronze, 10R4/10 over yellow, 7.5Y8/10 to bronze, 10R5/8 over yellow, 7.5Y8.5/10. |
| Reverse of petals. | Light bronze, 5Y7/8 to golden bronze, 5Y7/10. | Bronze, 2.5Y6/8 to yellow bronze, 2.5Y6/10. |
| Tonality from a distance. | Orange bronze | Bronze. |
| Discoloration. | Golden bronze | Light bronze. |

| | Wildfire | Detroit News |
|---|---|---|
| Petals: | | |
| Texture | Smooth | Smooth. |
| Appearance and form. | Open at base, broad keel, tapering to a hooded point. | Tubular to slightly open at base deeply keeled tapering to a hooded point. |
| Arrangement | Composite, whorled on a single receptacle. | Composite, whorled on a single receptacle. |
| Persistence | Resist shatter | Resist shatter. |
| Fragrance | Typical chrysanthemum. | Typical chrysanthemum. |
| Reproductive organs: | | |
| Stamen, anthers | None to 30 | None to 25. |
| Pollen | None to scant | None to scant. |
| Arrangement | Clustered in center of flower, if present. | Clustered in center of flower, if present. |
| Styles | Present both ray and disc florets. | Present both ray and disc florets. |
| Length | Short | Short. |
| Ovaries | At the base of petal attached to receptacle. | At the base of petal attached to receptacle. |
| Plant: | | |
| Form | Herbaceous | Herbaceous. |
| Growth | Upright | Upright. |
| Height | 36″ | 43″. |
| Spread | None | None. |
| Foliage: | | |
| Top side | Dark green, 10GY3/4 | Dark green, 10GY2/4. |
| Size | 7¼″ long, 3¾″ wide | 6½″ long, 4″ wide. |
| Quantity | Numerous | Numerous. |
| Shape | Spatulate lobed | Spatualte lobed. |
| Texture | Smooth | Smooth. |
| Ribs and veins | Prominent | Prominent. |
| Edge | Deeply indented | Deeply indented |
| Serration | Very slight | Finely serrated. |
| Underside | Light green, 10GY5/4 | Light green, 7.5GY4/4. |
| Stipules | Prominent | Rudimentary. |

We claim:

1. A new and distinct cultivar of chrystanthemum characterized generally by its unique bronze color and its capability of being grown either as a standard cut flower or as a pot mum, and characterized particularly as to uniqueness when grown as a standard and when compared with the cultivar Detroit News by its longer peirod of value, approximately ¼″ larger flowers, broader, flatter and less tightly incurved petals, more orange bronze color, longer keeping quality, approximately 7″ shorter growth habit, greater color retention under high temperature, high light conditions, fading to a darker, smoother, more attractive golden bronze color than the faded color of Detroit News under identical conditions, somewhat lighter colored and less brittle foliage, and its more prominent stipules; and which is further characterized as to uniqueness when grown as a pot mum and when compared with the pot mum Orange Bowl by its one week earlier response, more intense orange bronze flower color, more incurved flower, approximately ¼″ larger flower in the opening stage of development but smaller when fully expanded, larger and more deeply indented foliage with less serration of the leaf margin, more prominent stipules, shorter bench life, and its more efficient timing thereby providing a saving in crop time and bench space.

No references cited.

ROBERT E. BAGWILL, Primary Examiner